(12) United States Patent
Zarkh et al.

(10) Patent No.: US 8,126,241 B2
(45) Date of Patent: Feb. 28, 2012

(54) METHOD AND APPARATUS FOR POSITIONING A DEVICE IN A TUBULAR ORGAN

(76) Inventors: Michael Zarkh, Givat Shmuel (IL); Moshe Klaiman, Gadera (IL); Rami Evron, Tel Aviv (IL)

( * ) Notice: Subject to any disclaimer, the term of this patent is extended or adjusted under 35 U.S.C. 154(b) by 993 days.

(21) Appl. No.: 11/909,701

(22) PCT Filed: Mar. 31, 2005

(86) PCT No.: PCT/IL2005/000360
§ 371 (c)(1),
(2), (4) Date: Apr. 10, 2008

(87) PCT Pub. No.: WO2006/103644
PCT Pub. Date: Oct. 5, 2006

(65) Prior Publication Data
US 2008/0247621 A1    Oct. 9, 2008

(51) Int. Cl.
*A61B 6/03*    (2006.01)
(52) U.S. Cl. ......... 382/131; 382/294; 600/425; 600/427
(58) Field of Classification Search .......... 382/128–132, 382/294; 600/424–427, 431–435
See application file for complete search history.

(56) References Cited

U.S. PATENT DOCUMENTS

| | | | |
|---|---|---|---|
| 4,263,916 A | 4/1981 | Brooks et al. | |
| 4,889,128 A | 12/1989 | Millar | |
| 5,089,005 A | 2/1992 | Harada | 606/194 |
| 5,175,773 A | 12/1992 | Garreau et al. | |
| 5,203,777 A | 4/1993 | Lee et al. | |
| 5,207,226 A | 5/1993 | Bailin et al. | |
| 5,289,373 A | 2/1994 | Zarge et al. | |
| 5,446,800 A | 8/1995 | Briggs et al. | |
| 5,583,902 A | 12/1996 | Bae | |
| 5,699,799 A | 12/1997 | Xu | |
| 5,718,724 A | 2/1998 | Goicoechea et al. | |
| 5,729,129 A | 3/1998 | Acker | |
| 5,732,707 A | 3/1998 | Widder et al. | |
| 5,734,384 A | 3/1998 | Yanoff et al. | |
| 5,840,025 A | 11/1998 | Ben-Haim | 600/424 |
| 5,912,945 A | 6/1999 | Da Silva | |
| 5,978,439 A | 11/1999 | Koppe et al. | |
| 6,027,460 A | 2/2000 | Shturman | |
| 6,047,080 A | 4/2000 | Chen et al. | |

(Continued)

FOREIGN PATENT DOCUMENTS

DE    10047314 A1    4/2001

(Continued)

OTHER PUBLICATIONS

Zarkh et al., Three-dimensional reconstruction and analysis of coronary vessels: the CardioOp-B system, 2004, Proceedings of Cars 2004, International Congress Series 1268, p. 1367.*

(Continued)

*Primary Examiner* — Edward Glick
*Assistant Examiner* — John Corbett

(57) ABSTRACT

An apparatus and method for detecting, tracking and registering a device within a tubular organ of a subject. The devices include guide wire tip or therapeutic devices, and the detection and tracking uses fluoroscopic images taken prior to or during a catheterization operation. The devices are fused with images or projections of models depicting the tubular organs.

25 Claims, 6 Drawing Sheets

U.S. PATENT DOCUMENTS

| | | | |
|---|---|---|---|
| 6,094,591 A | 7/2000 | Foltz | |
| 6,148,095 A | 11/2000 | Prause et al. | |
| 6,167,296 A | 12/2000 | Shahidi | 600/427 |
| 6,190,353 B1 | 2/2001 | Makower et al. | |
| 6,195,577 B1 | 2/2001 | Truwett et al. | |
| 6,231,518 B1 | 5/2001 | Grabek et al. | 60/508 |
| 6,231,546 B1 | 5/2001 | Milo et al. | |
| 6,233,476 B1 | 5/2001 | Strommer et al. | |
| 6,246,898 B1 | 6/2001 | Vesely et al. | |
| 6,249,695 B1 | 6/2001 | Damadian | |
| 6,290,673 B1 | 9/2001 | Shanley | |
| 6,301,498 B1 | 10/2001 | Greenberg et al. | |
| 6,317,621 B1 | 11/2001 | Graumann | |
| 6,332,034 B1 | 12/2001 | Makram-Ebeid et al. | |
| 6,334,864 B1 | 1/2002 | Amplatz et al. | |
| 6,351,513 B1 | 2/2002 | Bani-Hashemi | |
| 6,370,417 B1 * | 4/2002 | Horbaschek et al. | 600/424 |
| 6,381,350 B1 | 4/2002 | Klingensmith | |
| 6,381,483 B1 | 4/2002 | Hareyama et al. | 600/407 |
| 6,385,332 B1 | 5/2002 | Zahalka et al. | |
| 6,389,104 B1 | 5/2002 | Bani-Hashemi et al. | |
| 6,463,309 B1 | 10/2002 | Ilia | |
| 6,470,207 B1 | 10/2002 | Simon et al. | 60/426 |
| 6,501,848 B1 | 12/2002 | Carroll | |
| 6,503,203 B1 | 1/2003 | Rafter | |
| 6,505,064 B1 | 1/2003 | Liu et al. | |
| 6,535,756 B1 | 3/2003 | Simon et al. | |
| 6,539,127 B1 * | 3/2003 | Roche et al. | 382/294 |
| 6,544,178 B1 | 4/2003 | Grenon et al. | 60/443 |
| 6,544,230 B1 | 4/2003 | Flaherty et al. | |
| 6,577,889 B2 * | 6/2003 | Ichihashi | 600/425 |
| 6,669,635 B2 | 12/2003 | Kessman et al. | 60/437 |
| 6,669,645 B2 | 12/2003 | Narimatsu et al. | 600/490 |
| 6,709,444 B1 | 3/2004 | Makower | |
| 6,748,259 B1 | 6/2004 | Benaron et al. | |
| 6,990,368 B2 | 1/2006 | Simon | |
| 6,996,262 B2 | 2/2006 | Li et al. | |
| 2002/0016544 A1 | 2/2002 | Hareyama et al. | 600/411 |
| 2003/0032866 A1 | 2/2003 | Winter et al. | |
| 2003/0181809 A1 | 9/2003 | Hall et al. | |
| 2003/0199759 A1 | 10/2003 | Richard | |
| 2003/0208116 A1 | 11/2003 | Liang et al. | |
| 2003/0230313 A1 | 12/2003 | Alipour et al. | |
| 2004/0054248 A1 | 3/2004 | Kimchy et al. | 600/436 |
| 2004/0102697 A1 | 5/2004 | Evron et al. | |
| 2004/0136491 A1 | 7/2004 | Iatrou | |
| 2004/0152974 A1 | 8/2004 | Solomon | |
| 2005/0010105 A1 | 1/2005 | Sra | |
| 2005/0107688 A1 | 5/2005 | Strommer | 600/424 |
| 2005/0113686 A1 | 5/2005 | Peckham | |
| 2005/0222595 A1 | 10/2005 | Maschke | |
| 2006/0036167 A1 | 2/2006 | Shina | |
| 2006/0058647 A1 | 3/2006 | Strommer et al. | 600/424 |

FOREIGN PATENT DOCUMENTS

| | | |
|---|---|---|
| EP | 1005835 A1 | 6/2000 |
| EP | 0885594 B1 | 4/2003 |
| RU | 2119765 A | 10/1998 |
| WO | 9625881 A1 | 8/1996 |
| WO | 0158359 A1 | 8/2001 |
| WO | 0185030 A1 | 11/2001 |
| WO | 03096884 A3 | 11/2003 |
| WO | 2005008583 A3 | 1/2005 |
| WO | 2005020148 A1 | 3/2005 |
| WO | 2005031635 A1 | 4/2005 |
| WO | 2006033113 A3 | 3/2006 |
| WO | 2006061815 A1 | 6/2006 |
| WO | 2006117773 A1 | 11/2006 |

OTHER PUBLICATIONS

Baert et al., Three-dimensional Guide-wire Reconstruction from Biplane Image Sequences for Integrated Display in 3-D Vasculature, Oct. 2003, IEEE Transactions on Medical Imaging, vol. 22, No. 10, pp. 1252-1258.*

"Automatic Segmentation of the Coronary Artery Tree in Angiographic Projections," by Marc Schrijver and Cornelis H. Slump, published in Proceedings of ProRISC 2002 Nov. 28-29, pp. 449 and 451.

Bankman, I., "Handbook of Medical Imaging Progessing and Analysis," pp. 359-374 (2000).

Close, R., et al., "Accuracy Assessment of Layer Decomposition Using Simulated Angiographic Image Sequences," IEEE Transactions on Medical Imaging, vol. 20No. 10, pp. 990-998, 2001.

Eiho, S., et al., "Preoperative and intraoperative image processing for assisting endovascular stent grafting,"Informatics Research for Development of Knowledge Society Infrastructure, 2004.

Garraeu, M., et al., "A knowledge—based approach for 3-D reconstruction and labeling of vascular networks from bi-plane Angiographic projections," IEEE transactions on medical imaging, vol. 10, No. 2, 1991.

Nelson, T.R., et al., "Three-dimensional ultrasound imaging" Ultrasound in Medicine and Biology, vol. 24, No. 9, pp. 1243-1270, 1998.

Penney, G.P., et al., "A Comparison of Similarity Measures for Use in 2-D-3-D Medical Image Registration," IEEE Transactions on Medical Imaging, IEEE Service Center, vol. 17, No. 4, pp. 586-595, 1998.

Russakoff, D.B.,et al., "Intensity-based 2D-3D spine image registration incorporating a single fiducial marker," Academic Radiology, vol. 12, No. 1, pp. 37-50, 2004.

Srihari, R., et al., "Image background search:combining object detection techniques with content-based image retrieval (CBIR) systems," Content-Based Access of Image and Video Libraries, 1999.

* cited by examiner

METHOD AND APPARATUS FOR POSITIONING A DEVICE IN A TUBULAR ORGAN

RELATED APPLICATIONS

The present invention relates to international patent application serial number PCT/IL01/00955 titled "METHOD AND SYSTEM FOR POSITIONING A DEVICE IN A TUBULAR ORGAN" filed on Oct. 15, 2001.

BACKGROUND OF THE INVENTION

1. Field of the Invention

The present invention relates to medical systems in general, and to a method and apparatus for positioning and presenting a device in tubular organs, in particular.

2. Discussion of the Related Art

Interventional cardiology procedures are becoming increasingly important in the treatment of physiological abnormalities such as lumen stenosis or aneurysm. For example, in order to treat a stenotic coronary artery, it is often required to inflate a balloon, apply an atherectomy or thrombectomy device and place a stent (prosthesis) at a diseased artery site. In this example, the devices are either a guide wire or a therapeutic intravascular device, such as a balloon, a stent, an atherectomy, or a thrombectomy device. On the therapeutic stage of the catheterization procedure the physician inserts a guide wire, mounting it distally of the stenotic vessel and then delivers the therapeutic device (balloon or stent) to the stenotic location. In cases of difficult morphology of the vessel the guide wire insertion becomes a challenging task even for skilled physicians. Furthermore, navigation of the guide-wire in anatomies such as bifurcations and branches is always a challenging task. In order to accurately locate the device within the artery, fluoroscopic x-ray images are taken during the navigation of the guide-wire into position. In addition, the subject is often injected with contrast material which facilitates the view of the arteries in the image as well. Real-time assistance in navigation and localization of the guide-wire could prove very helpful in such cases and may reduce contrast material injection. Accurate deployment of the therapeutic device is another important factor of therapy success. It is known that in some of cases, deployment of a therapeutic device such as a stent is not optimal, an indication to that is a necessity to deliver an additional stent to cover the stenotic segment. The issue of the device location becomes even more important when drug-eluting stents are considered. A capability of automatically and accurately locating a device without injecting additional contrast materials, yields certain benefit. The novelty of the proposed navigation system is that it does not require additional equipment beyond the already used guide wire and device. All involved tasks are carried out automatically without altering the standard flow of a catheterization procedure.

Yet another interventional radiology procedure where accurate positioning of a device is crucial for achieving good quality results is a bi-ventricular pacing procedure. By placing a pacing lead in different positions in the coronary vein tree and checking the heart response to the electric impulse, the physician chooses the optimal position and deploys the lead in the chosen position. The problem is to identify each checked location and provide a method of automatic navigation to the chosen one.

In the context of this invention, the term "device" refers interchangeably to a guide wire tip and to a therapeutic device. When the tubular organ is an artery, the therapeutic device is an intravascular therapeutic device, such as a stent or a balloon. The location of a catheter tip, guide wire tip or intravascular therapeutic device with reference to surrounding arterial anatomy is monitored by X-ray fluoroscopy. When necessary, the angiographer releases a contrast material, such as iodine solution, from the catheter tip. The contrast material is carried from the catheter tip by the blood flow, and an X-ray image of the arterial anatomy in the vicinity of the catheter tip is obtained, showing both the artery and the catheter tip. Based upon the obtained X-ray image, the guide wire is advanced until the desired arterial anatomy is reached. Usually, in order to treat the artery, the tip of the guide wire should pass through the diseased region to the distal end of the diseased region. Subsequently, an intravascular device is mounted on the guide wire and brought to the diseased arterial region. Monitoring the location of the therapeutic device inside the artery is performed by following the movement of radio-opaque markers sliding along the guide wire that flanks the device. The markers indicate the position of the device in reference to the guide wire.

Most of the known navigation methods use special equipment for therapeutic device localization. Such equipment can be based on optical or electro magnetic tracking principles using sensors and transducers for measuring position of the device in some reference coordinate system. In order to achieve acceptable results the imaging system and the tracking systems must be well calibrated presenting the image and location of the device in common coordinate system. Additional equipment increases the cost of procedure, makes it more complicated, and requires accurate calibration. Another type of methods for device positioning uses mechanical tools which confine the right positioning for the device. These methods serve specific types of treatments and therefore are not universal. International patent application publication number WO 96/25881 titled METHOD FOR ULTRASOUND GUIDANCE DURING CLINICAL PROCEDURES published on Aug. 29, 1996 describes a method for combining a geometric localization of a tool with acquired ultrasound images. However, ultrasound modality cannot be applied for some organs, such as coronary arteries. WO 96/25881 further describes a method for guiding a tool to reach an organ without intersecting other organs. WO 96/25881 does not relate to navigating a tool located inside a tubular organ towards a pre-defined position within the tubular organ. The target and surrounding organs are required to be visible in images acquired throughout the insertion. Thus, the main difficulty of the registration, which is an essential step in data fusion, is solved by using additional equipment—the organs are imaged by ultrasound throughout the insertion. The last solution is not valid for the case of X-ray angiography, for example.

Another publication demonstrating the usage of Ultrasound technology for real-time imaging of devices, is International patent application publication number WO 01/58359 titled ULTRASONIC IMAGER published on Aug. 16, 2001. WO 01/58359 discloses an ultrasound imaging system that superimposes sectional views created from volumetric ultrasound data, and the location data for an intervention device, such as a catheter as obtained from external sensors. The position of an interventional medical device may be shown, in one or more views, relative to organs and tissues within a body as the interventional device is moved. The interventional device positional data is updated continuously and is superimposed on tissue images that may be updated less frequently, resulting in real-time or near real-time images of the interventional device relative to the tissues. The superimposed images permits medical personnel to perform procedures such as angiograms with minimal or no exposure of patients to x-rays and contrasting dye. The current ultrasound image where catheter appearance is enhanced by vibration mechanism or by brightening technique is supposed to be aligned with a reference image. The combination of the two images is carried out by straightforward overlay. However, as mentioned above, ultrasound technology is not applicable to all organs, and especially to coronary arteries, since the technology does not compensate for changes in imaging conditions and for movement of organs.

U.S. Pat. No. 6,389,104 entitled FLUOROSCOPY BASED 3-D NEURAL NAVIGATION BASED ON 3-D ANGIOGRAPHY RECONSTRUCTION DATA discloses a method for detection of a moving catheter in a lower quality fluoroscopic image and presenting the catheter with high quality 3D reconstructed vascular structure. The suggested method assumes complete information of the imaging perspective geometry both on the diagnostic stage when the 3D model is generated by using images captured by a rotational angiography and on the therapeutic stage of fluoroscopy guided navigation of catheter. Under such restrictive and practically problematic assumptions, one of the central problems of image registration is reduced to essentially carrying out known transformations. Additionally, the suggested method is not applicable to moving organs, such as arteries whose shape changes with the heart beat cycle. Yet another drawback of the method is that the catheter is identified in low quality fluoroscopic images by usage of special intensity modulated catheter. Thus, the method requires complete information of the imaging conditions, a static scene and a special catheter, making it inapplicable for standard coronary angioplasty.

There is therefore a need in the art for a system that will generate a model of a body area including tubular organs, during a diagnostic stage, and will use the generated model for purposes of automatic identification and tracking of a device located inside a tubular organ during a therapeutic stage. It is desirable that the system will use x-ray imaging during the therapeutic stage, although most tubular organs, such as vessels are not visible in x-ray images. The system should not require additional equipment in excess of the equipment currently required for the relevant types of procedures. It is also desirable that the system will perform automatic registration of images between images captured during a diagnostic step and images captured during a therapeutic stage overcoming geometric distortions and differences in content. The system should automatically register the images, determine the location of the device, and will display the device, along with relevant measurement data, together with reference images of the body area or the reconstructed model thereof. The system should minimize the need for harmful contrast material injections and radiations to the subject.

SUMMARY OF THE PRESENT INVENTION

It is an object of the present invention to provide a novel method for automatic registration of one or more captured images of a device within a tubular organ of a subject, with a reference source presenting a body area of the subject containing the tubular organ, the method comprising the steps of generating a two-dimensional reference image of the reference source; generating one or more first background images of the captured image and one or more second background images of the reference image; generating a tubular organ reference image from the reference image; generating a device image from the captured image; performing registration between the device image and the vessel reference image, based on constrained correlation; and fusing information from the captured image and from the reference source. The tubular organ is not visible on the captured image. The constrained correlation uses a last injection image, the constrained correlation step comprising the steps of performing a constrained correlation between the captured image and the last injection image, and performing a constrained correlation between the reference image and the last injection image. The tubular organ reference image or the first background image or the second background image is prepared using an improved vessel resemblance operator. The reference source comprises one or more two-dimensional or three-dimensional models, or one or more two-dimensional or three-dimensional images. The fused information comprises a fused image, containing one or more elements from the captured image and one or more elements from the reference source. The device is a guide wire or a therapeutic device. The image is an x-ray image. The tubular organ is a vessel. The reference image is an image which participated in constructing a model of the body part, or it is a synthetic image produced from the reference source. The synthetic image is a projection of the reference source onto a plane. The step of generating the device image comprises the steps of detecting of the device within the tubular organ; and calculating a binarized image depicting the device. The detecting of the device comprises the steps of identifying the device and tracking the device. The method further comprising the step of localizing the device detected within the one or more images with one or more images of the reference source. The method further comprising a steps of assessing a disease; providing the user with a recommendation for the type and location of the device; and receiving the user's choice of designated type and location of the device. The combined information comprises numerical data. The numerical data is the distance between the location of the device in the captured image and the designated location of the device. The combined information comprises input to a feedback control system. The method further comprising the step of displaying the device detected within the one or more captured images with one or more images of the model, on a display device. The method further comprising the step of transmitting the coordinates of the detected device to a feedback control device. The device is a guide wire. Detecting the guide wire within the captured image comprises the steps of performing a binarization of the captured image and performing a coarse registration of the binarized image to a reference image or to a last injection image. Tracking the guide wire within the image comprises the steps of performing a parameterization of the pixels in a reference image showing the tubular organ, according to a set of parameters; applying the parameterization to the pixels of the at least one captured image, thus creating a parameterized image containing pixels; sorting the pixels contained in the parameterized image; and segmenting the guide wire tip by analyzing the sorted pixels of the parameterized image. The set of parameters comprises the shortest distance between a pixel in the reference image and a centerline of the tubular organ viewed in the reference image, and the index of the pixel in the centerline which is closest to the pixel in the reference image. Tracking the device within the image comprises the step of optimal path search on the captured image. The device is a therapeutic device, or a pacing lead. The identifying step comprises thresholding most pixels in the captured image, thus receiving at least one cluster; assigning a score to each at least one cluster; assigning a score to each pair of clusters. If the highest score assigned at step c to a pair of clusters exceeds a predetermined threshold, selecting the pair of clusters as the markers. The further comprising:

repeating the abovementioned steps for a second captured image; creating quartets of clusters, where the first pair of clusters is taken from the clusters received from the captured image, and the second pair of clusters is taken from the second captured image; assigning a score to each quartet of clusters, the score comprising the score of each pair and a similarity factor between the pairs; assigning a second score to each pair of clusters in the captured image, based on the scores for all quartets in which the pair of clusters participates; assigning a second score, to each pair of clusters in the second captured image, based on the scores of all quartets in which the pair of clusters participates; and if the highest score assigned at the last step to a pair of clusters exceeds a predetermined threshold, selecting the pair of clusters as the markers in the captured image or in the second captured image. The steps are adapted and executed with additional captured images until a pair of clusters is selected. The tracking step comprises using correlation surfaces between two consecutive captured images and one or more movement consistency criterion. The method further comprising the step of monitoring an image sequence acquisition and parameters. The method further comprising the step of injecting the subject with contrast material. The method further comprising the step of automatically determining a last injection image. The method further comprising the step of receiving the reference source, or the step of generating the reference source. The method further comprising the step of planning a feedback control. The model is constructed from two or more images of the subject acquired from at least two different perspectives. The method further comprising a step of determining the best perspectives for capturing images for navigating the device within the tubular organ. The method further comprising the steps of: assessing a disease; providing the user with a recommendation for the type or location of the device; and receiving the user's choice of designated type or location of the device. The tubular organ reference image is prepared using an improved vessel resemblance operator. The method is used during a catheterization procedure, or ventricular pacing, or an angioplasty procedure.

Another aspect of the invention relates to an apparatus for automatic registration and detection of one or more captured images of a device within a tubular organ of a subject, with a reference source presenting a body area of the subject containing the tubular organ, and tracking of the device within the tubular organ, the apparatus comprising: one or more detection components for detecting a device within the tubular organ of the subject; and one or more registration components for registering the captured images with a model of a body part containing the tubular organ. The captured image is an x-ray image. The tubular organ is a vessel. The device is a guide wire or a therapeutic device. The detection components comprise one or more guide wire detection components or one or more therapeutic device detection components. The guide wire detection components comprise one or more binarization components, or one or more parameterization component, or one or more segmentation components or one or more vector presentation component. The device detection components comprise one or more identification components, or one or more tracking components. The apparatus further comprising a diagnostic component comprising a three dimensional model builder, or a perspective choosing component, or a device selecting component.

Yet another aspect of the disclosed invention relates to a computer readable storage medium containing a set of instructions for a general purpose computer, the set of instructions comprising one or more detection components for detecting a device within the tubular organ of the subject; and one or more registration components for registering the captured images with a model of a body part containing the tubular organ.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENT

Figure 1:
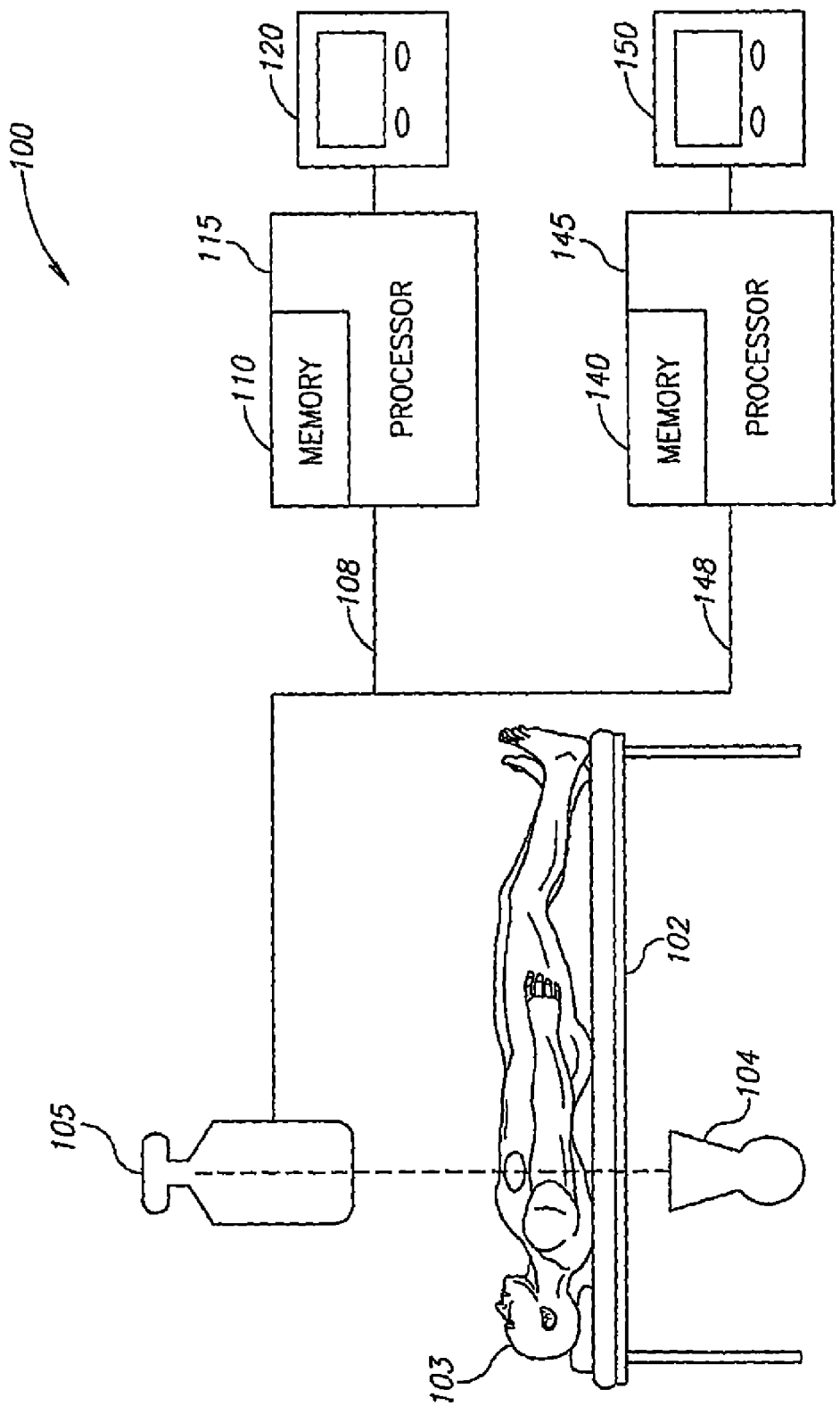
FIG. 1 is an illustration of a typical environment in which the proposed invention is used.

The disclosed invention presents an apparatus and method for automatic detecting and tracking of a device within a tubular organ, such as an artery, a blood vessel, or a urethra of a subject. In the context of the disclosed invention, "device" relates either to a guide wire tip, a catheter tip, or a therapeutic device. When the tubular organ under discussion is an artery, the therapeutic device is usually an intravascular therapeutic device, such as a stent, a balloon, a pacing lead, or the like.

The present invention can be implemented, but is not restricted to in the following procedures: catheterization procedure, bi-ventricular pacing, coronary angiography, coronary angioplasty, peripheral angiography, peripheral angioplasty, carotid angiography, carotid angioplasty, neuro angiography/plasty, biliary imaging or intervention, and the like.

In a preferred embodiment, the method of the present invention employs a diagnostic stage and a therapeutic stage. During the diagnostic stage, a 2-dimensional or 3-dimensional model of the relevant body area, including the tubular organs is constructed from images of the subject. The 2-dimensional or 3-dimensional images are acquired by an x-ray machine, Computerized Tomography (CT), or any other like modality. In a preferred embodiment of the disclosed invention, in addition to constructing a model of the body area, a suitable therapeutic device and location for the therapeutic device within the tubular organ are determined and marked during the diagnostic stage. The therapeutic device type and location are determined in order to provide the patient with appropriate treatment, taking into consideration the morphology and the dimensions of the diseased area. Additionally, the system marks preferred C-arm perspectives to be employed during the insertion of the device. In an alternative embodiment, the system uses a model received from an external source rather than generating the model. In another preferred embodiment, the system determines a feedback control for a system that automatically controls the advancement or the shape of the device at a therapeutic stage.

In another preferred embodiment, the method employs a therapeutic stage only, during which the system uses the model received or generated during the diagnostic stage, together with current x-ray images taken during the therapeutic stage to locate, track and display a device inside the tubular organ. During a typical therapeutic stage, a guide wire having a tip is navigated to the required area of the body. Then a therapeutic device is mounted on the guide wire and led to a required location by sliding along the guide wire. The device is located and tracked by following the movement of radio-opaque markers located thereon, in a series of current x-ray images. In an alternative embodiment, the markers are not opaque but are otherwise visible using alternative means or modalities. Then, the current images and a 2-dimensional projection of the model, employing substantially the same projection angle and parameters as the current images, are superimposed thus showing simultaneously the device and the region of the artery. The device is advanced in the artery towards the desired region, based upon a comparison of the present location of the device in the artery and the desired location, if marked. This process is repeated until the device appears in an image in the region of the artery where the operator determined it should be located. When necessary, contrast material is released from the catheter tip and a current image showing the artery and the device is obtained.

The main difficulty in locating and displaying the device as captured in the current image in conjunction with the model, is that the two sources of information, i.e., the model and the current image are different both in content and in geometry. In order to fuse and present contents from multiple sources on one image, the sources should be registered with each other, i.e. be translated into a common coordinate system. The common coordinate system can be the coordinate system of one of the sources, translating the coordinate systems of the other sources, or a different coordinate system, in which case all sources should be translated to the common coordinate system.

The difference in content stems from the reference model containing organs only, since the device was not present at the time the model was generated, and the current images mostly containing the device only. The current images mostly contain the device only, since tubular organs are shown only on images taken after injecting the subject with contrast material. The differences in the geometry stem both from the different imaging characteristics, such as C-arm positions, intensity, and the like, and the difference in the shape of the tubular organs caused by the presence of the device therein. In a preferred embodiment this twofold gap is bridged by using a mediating image, captured during the therapeutic stage with contrast material injection, hereby referred to as last injection image. This mediating image has common content with the model, since it shows the tubular organs. In particular, it has common content with the images participating in the construction of the model, or with an appropriate 2-dimensional projection of the model. On the other hand the mediating image has imaging conditions which are similar to those of the current image, although the content is generally different due to the absence of the tubular organs in the current image. Thus, the presented method preferably involves a two-stage registration process—from the current image to the mediating image, and from the mediating image to a reference image participating on the model or a projection thereof.

Referring first to FIG. 1, showing a preferred embodiment in which the present invention is used, generally referenced as 100. System 100 is used for positioning a catheter or intravascular device at a desired location within an artery in accordance with one exemplary embodiment of the invention. The system comprises a table 102 upon which a patient 103 lies. An X-ray source 104 is located under table 102 for projecting X-rays through patient 103 to an X-rays camera 105 located above table 102, diametrically opposite X-ray source 104. X-ray camera 105 generates video signals or digital images 108, for example in DICOM format representing one or more X-ray images of patient 103. Video signals or digital images 108 are stored in a memory 110 of a processor 115. Images captured by X-ray camera 105 may be viewed on a display device 120, such as a monitor or any other display device, either in real-time or after being retrieved from the memory 110. The images can be captured either at a diagnostic stage, or at a therapeutic stage, or both. In an alternative embodiment, the x-ray source and camera can be placed in other locations. In yet another alternative, the imaging equipment can be another modality, such as Computerized Tomography, Magnetic Resonance, or the like. Processor 115 is preferably a computing platform, such as a personal computer, a mainframe computer, or any other type of computing platform that is provisioned with a memory device 110, a CPU or microprocessor device, and several I/O ports (not shown). Alternatively, processor 115 can be a DSP chip, an ASIC device storing the commands and data necessary to execute the methods of the present invention, or the like. Processor 115 can further include a storage device (not shown), storing the device guidance application. The device guidance application is a set of logically inter-related computer programs and associated data structures that interact to detect and track a device in an x-ray sequence, and register the frames with a pre-acquired 3-dimensional model of the relevant body area. The device guidance application is detailed in association with FIG. 4 below. The computerized steps of the proposed method can be implemented on processor 115 and the output displayed on display device 120. Alternatively, the computerized steps of the proposed method can be implemented on a dedicated processor 140, receiving video signals or digital data 148 from X-ray camera 105, and comprising a memory device 145. The output of the method can be displayed on a dedicated display 150.

Figure 2:
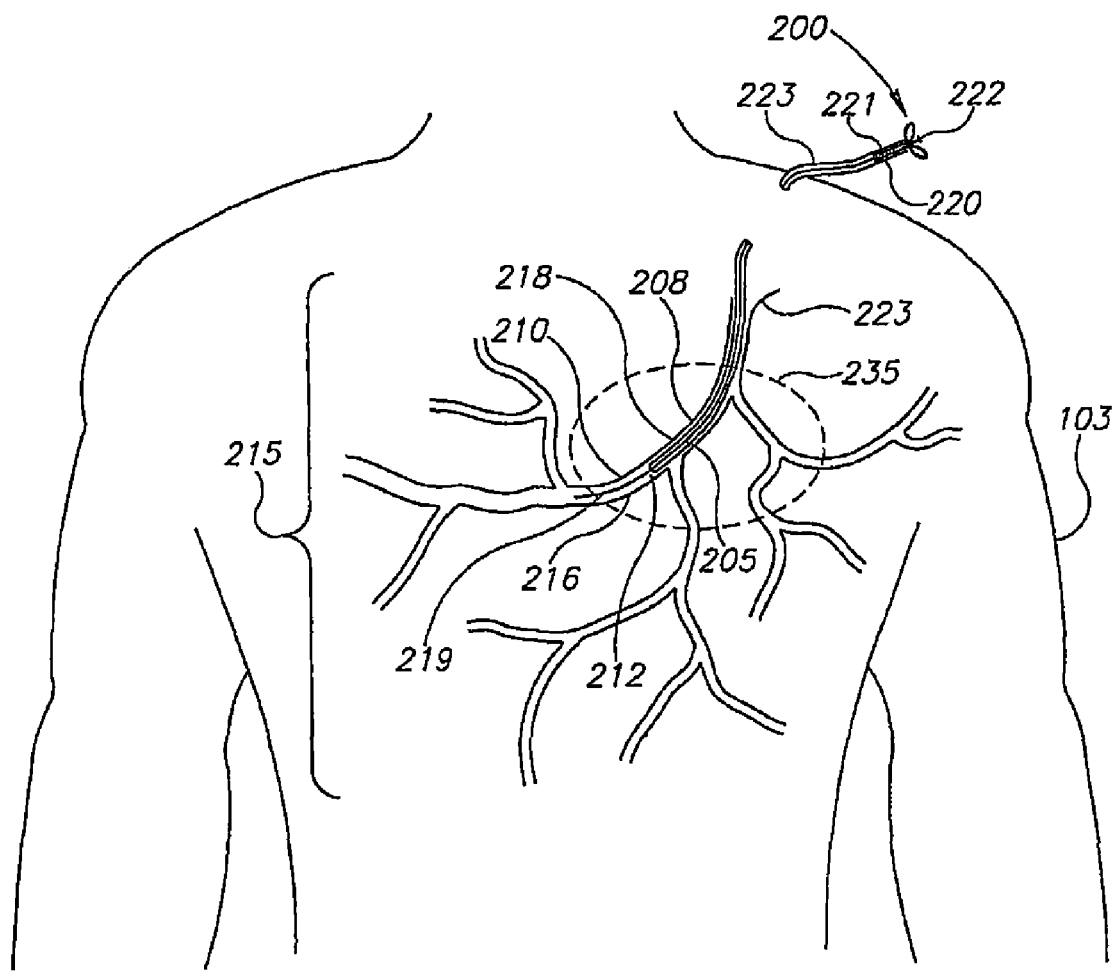
FIG. 2 is an illustration of a device being navigated through an arterial system, in accordance with a preferred embodiment of the present invention.

Referring now to FIG. 2, showing a catheter 200, having a tip 205 positioned at an aperture 212 of an artery 210 that is a part of an arterial tree 215 of patient 103. Catheter 200 may be used to deliver an intravascular device 218 mounted on a guide wire 216 to a desired location 219 within artery 210. Catheter 200 is connected to a reservoir 220 containing a radio-opaque liquid 221 such as an iodine solution that is conducted from reservoir 220 to catheter tip 205 and released from catheter tip 205 as required by depressing a piston 222. When contrast material 221 is released from catheter tip 205, an image is obtained of the arterial tree in area 235 around catheter tip 205 by X-ray camera 105. Based upon the obtained image, catheter tip 205 is brought to arterial system 215, which contains artery to be treated 210. Then, guide wire 216 is extended from catheter tip 205 and brought to the diseased region within an artery 219 using fluoroscopy and short injections of contrast material. After positioning of guide wire 216 within artery 210, a device 218 is inserted into artery 210 towards region to be treated 219 along guide wire 216.

Figure 3:
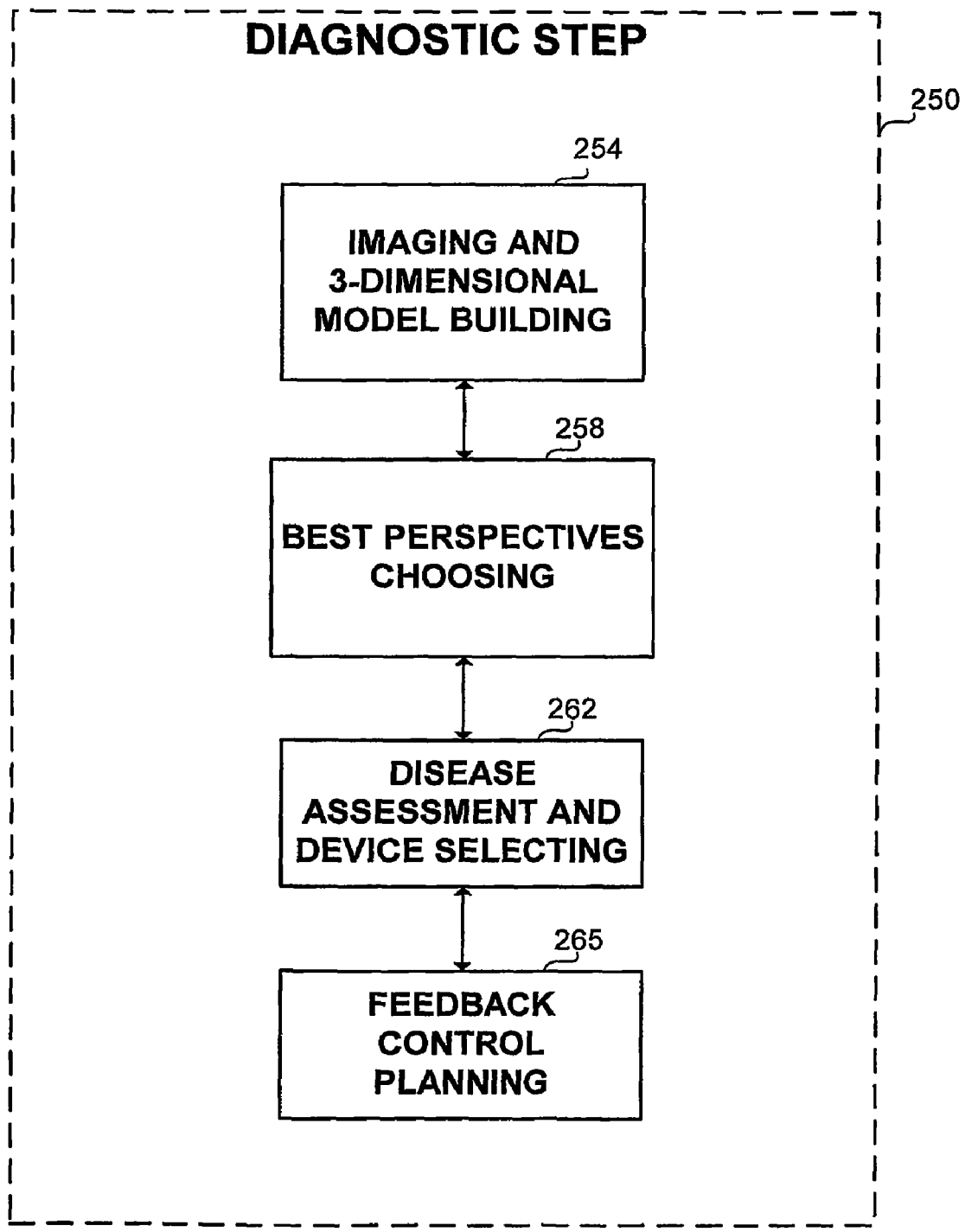
FIG. 3 is a block diagram describing the operational steps associated with a diagnostic step, in accordance with a preferred embodiment of the present invention.

The method of the present invention involves two groups of steps, a diagnostic step group and a therapeutic step group. Referring now to FIG. 3, showing a flowchart of the diagnostic step group, generally referenced as 250, in accordance with the method of the present invention. Step group 250 comprises step 254, in which the vessels are imaged with a C-arm X-ray angiographer from different perspectives, and a 3-dimensional reconstruction of the tubular organ is built using two or more 2-dimensional images. The process of reconstruction includes analysis of the vessel tree surrounding the stenosis and calculation of relevant information, for example vessel centerline, boundaries, diameters and so on. This step is further disclosed in Applicant's International patent application publication number WO 01/85030 titled SYSTEM AND METHOD FOR THREE-DIMENSIONAL RECONSTRUCTION OF AN ARTERY published on Nov. 15, 2001. Then, at step 258 the best perspectives for viewing the artery during a catheterization are determined. The perspectives comprise the position of the C-arm which will yield the best view of the artery. At step 262, based on the reconstruction and associated measurement data, the physician assesses the severity of the disease and select the most appropriate type of therapeutic device. The system can offer, given enough device information, a default location for the device deployment, though the physician can interactively choose a desired location for the device. At step 265, additional information, useful for the navigation of the device along the artery, for example landmarks, such as branching points or points with maximal curvature, or rules determining a feedback control for advancement and deployment of the device is also provided. This information includes also a complexity index comprising local curvatures, tortuosity, and locally preferable C-arm orientation for navigation, i.e. projection minimizing local foreshortening. Preferable C-arm orientation can be selected from the perspectives used during the 3D reconstruction or as overall optimal orientation. Step 254 is performed first, and steps 258, 262, 265 are performed following step 254, in any required order, or simultaneously.

In an alternative embodiment, the model building step is skipped, and the 3-dimensional model of the artery is acquired from an external source, and the perspectives determination and device selection steps are skipped. In a yet another alternative, the steps of the perspectives determination and device selection are performed on a 3-dimensional model of the artery as received from an external source.

Figure 4:
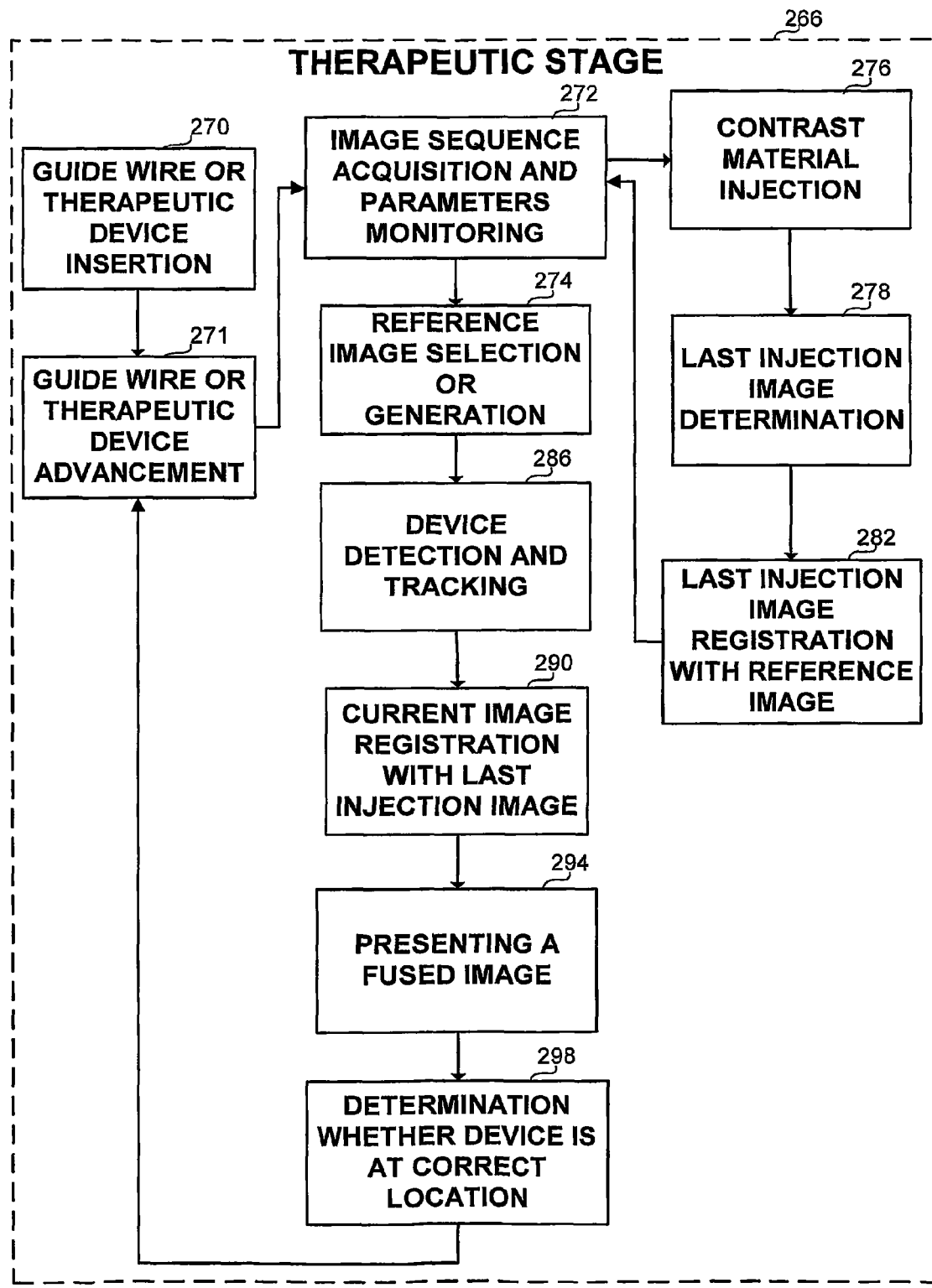
FIG. 4 is a block diagram describing the operational steps associated with a therapeutic step, in accordance with a preferred embodiment of the present invention.

Referring now to FIG. 4, showing a flowchart of the therapeutic group of steps, generally referenced as 266, in accordance with the method of the present invention. Therapeutic step group 266 is employed during a catheterization or another operation, such as an intravascular operation. Step group 266 comprises step 270, in which a guide wire is introduced to the artery so that its tip is placed distally to the diseased vessel segment. A therapeutic device is preferably mounted on the guide wire and advanced along the wire to the required location. The therapeutic device is usually a balloon or a balloon and a stent, sliding along the guide wire. When the balloon or the stent or both reach the designated position it is inflated or deployed. At step 271, the guide wire or the device is advanced within the tubular organ towards the required location. At step 272 the system monitors in real-time the acquisition of cine/fluoroscopic sequences, the C-arm parameters and ECG signal. The ECG signal serves as a tool for gating, i.e. choosing an image frame from the video stream being in the same phase of the heart beat cycle as the reference image. The gated frame is the highest correlated frame with the reference image. If the required update rate is higher than once every heart beat, the relevant images are assigned with a synchronization tag. If an ECG signal is not available, the synchronization parameter can be deduced based on correlation criteria between the captured images and the reference images. At step 274, a reference image is selected or generated. If the current C-arm orientation is close to the orientation of one of the images that participated in the 3-dimensional model reconstruction, this image is selected by the system as a reference image. If no such image exists, a synthetic reference image is constructed by means of projecting the 3-dimensional model to the imaging plane of the current C-arm orientation. At step 276, which is optional and occurs according to the physician's discretion, the subject is injected with contrast material, and at step 278, contrast material injected images are determined, requiring that all acquired sequences preferably go through analysis of the iodine injection. For example, each frame in each sequence passes a preprocessing enhancing the vessels, and receives a score indicating the presence of vessel-like features. Analyzing the scores as a function of time, the method identifies iodine injection sequences. Using the ECG signal monitored at step 272, a frame synchronized with the reference frame is chosen. The chosen frame serves as a last injection image for the current C-arm orientation. When an ECG signal is not available, the last injection frame is determined using, for example, a correlation criterion between each frame and the reference image. The last injection image for every C-arm orientation used in the navigation process is stored in the memory and is retrieved when C-arm returns to the orientation previously used in the navigation process. Step 278 is performed in accordance with step 272 at which the sequences are captured. At step 282, the last injection image is registered with the reference image. This is facilitated by the contrast material showing the arteries. Steps 278 and 282 do not require real time implementation. Rather, they could be performed in near real time. Upon completion of step 282 the previous last injection image is substituted with the new one.

At the beginning of the navigation, a last injection image does not exist yet. Sometimes, the last injection image is not available for the whole procedure. Therefore, the current image is registered directly with the reference image. At step 286, the device, i.e., the guide wire tip or the markers on a therapeutic device is detected and tracked in real-time on the current image. The detection and tracking is different for a guide wire tip and for a therapeutic device. The processes for the detection and tracking are detailed below. At step 290, the current image is registered with the last injection image, or directly with the reference image. This step is also further detailed below. At step 294, the guide wire tip or the device, whose location was found at step 286 are fused and presented together with the reference image, on a combined image, thus providing a fused image of the artery, its surroundings and the device therein. Steps 290 and 294 are also performed in real-time, for each captured image. The fused presentation reduces the need for contrast material injections and provides assistance for accurate device deployment. At step 298, the system determines and presents the distance between the device and the designated location, as marked during the diagnostic stage, or the distance between the device and a known landmark designated during the diagnostic stage, such as a bifurcation point, maximal curvature point, or the like. In a preferred embodiment, the determined location of the device is sent as input to a feedback control system which automatically controls the advancement or the shape of the device. Steps 271, 272, 274, 286, 290, 294 and 298 are repeated until the physician determines that the device is properly located, and at a higher rate than steps 276, 278, and 282, which are performed according to the physician's discretion.

Optionally, the 3-dimensional model building is skipped, which requires the therapeutic step group to employ a 3-dimensional model received from an external source. In a case, if the best perspectives and device selection steps are skipped, the determination of the distance between the location of the device and its designated location is skipped as well.

Figure 5:
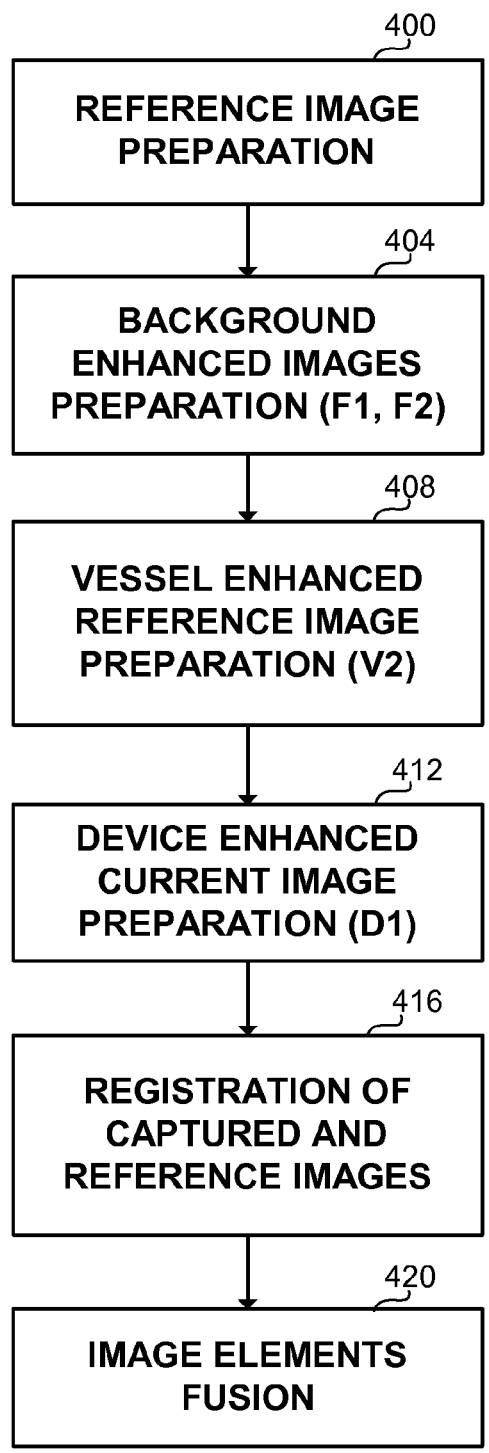
FIG. 5 is a flowchart of the registration method, in accordance with a preferred embodiment of the present invention.

Referring now to FIG. 5, describing in detail the registration task which is also integrated with the identification and tracking tasks of the method and apparatus. The registration presented in FIG. 5 is applicable when directly registering a current image to the reference image representing a reference source, or when incorporating a last injection image as a mediating image. In the latter case, two registrations are performed: between the last injection image and the current image, and between the reference image and the last injection image. Each registration is preferably implemented according to the FIG. 5. The registration scheme utilizes the principle of constrained correlation. Constrained correlation of two images I1 and I2 means applying a requirement for markers detected in the current image to be translated to a vessel in the reference image or in the last injection image, since the markers are attached to a device which is known to be inside a vessel. Similarly, registering the reference image with the last injection image an additional constraint requires a traced artery segment in the reference image to be translated to a vessel in the last injection image. Generally, constrained correlation involves the construction of a combined correlation surface from two correlation surfaces $$CC(I1,I2)=f(C(F1,F2),C(D1,V2))$$

This definition implies that a combined correlation surface $CC(I1,I2)$ between images I1 and I2 is a result of the combination of two correlation surfaces: $C(F1,F2)$ and $C(D1,V2)$, where F1 and F2 are consistent features existing in the background of images I1 and I2, and therefore $C(F1,F2)$ expresses the correlation between the background features, D1 is a device enhanced image and V2 is a vessel enhanced image. For a non-limiting example, the correlation surface combination might be an element-by-element multiplication of the two correlation matrices $CC(I1,I2)=C(F1,F2)\cdot C(D1,V2)$ Another example for the function $f$ combining the two correlation surfaces is a product of the first correlation matrix $C(F1,F2)$ with a binarized version of the second correlation surface:

$CC(I1,I2)=C(F1,F2)\cdot(C(D1,V2)>T)$. For clarity sake, the constrained correlation matrix between two images I1 and I2 is equal to the values of those pixels in the correlation matrix between the background features present in both images, for which the corresponding pixels in the correlation matrix between D1 and V2 exceed a certain threshold. The pixels in the constrained correlation score matrix, for which the correlation between D1 and V2 is below the threshold, are zeroed. For different registration tasks, involved with the navigation process, the images participating in the constrained correlation calculation can obtain specific forms, enhancing specific features.

FIG. 5 shows an exemplary registration task, performed as a stand-alone task of registering a single current image with a reference source. The reference source comprises a 2-dimensional or a 3-dimensional model of the body part, and the images used to construct the model. Unless otherwise mentioned, the method refers both to guide wire and to a therapeutic device. At step 400, a reference image is prepared out of the reference source, such as a model. The reference image I2 is, for example one of the images used to construct the reference model, or a projection of the model on the same plane as the current image. Then, at step 404, background enhanced images are prepared from the current image and form the reference image. The background enhanced images F1,F2 comprise consistent background elements captured in the two images, such as for example bones, or even the vessels (when the registration is between the reference image and the last injection image, which is not the case in the current example, and mentioned for the completeness of the description). The elements of the background are preferably enhanced using a gradient magnitude operator. Alternatively, the feature enhanced images are gradient vector field images, or Laplacian of Gaussian filtered images. At step 408 a vessel enhanced reference image V2 is prepared from the reference image. The vessel enhanced reference image is generated using a vessel resemblance operator. An improved vessel resemblance operator is detailed further below. At step 412 a specific device enhanced current image D1 is prepared from the current image I1. In the case of guide wire navigation a special filter is preferably applied for enhancement of thin dark lines. In the case of device navigation, the device enhanced image can be obtained by a dot-enhancing filter. When guide wire or device markers have been detected, image D1 can be constructed as a binary image depicting the found device. The generation of the binary image is further detailed in association with FIG. 6 below. At step 416, the registration itself between the current image I1 and the reference image I2 is performed using an implementation of the constrained correlation principle. In the case of direct registration of the current image with the reference image, the current image is preferably enhanced by explicit incorporation of the vessel model into it.

Registration between the current image and the last injection image is essentially similar to the registration between the current image and the reference image. At this step the registration between the reference image and the last injection image is already performed and the last injection image is preferably augmented by incorporating therein the vessel model translated from the reference image.

In the case of registration between the reference image and the last injection image, the reference image plays the role of I1 and the last injection image plays the role of I2. The feature images F1,F2 as well as image V2 are the vessel enhanced images (for example by vessel resemblance operator). The image D1 might be a binary image, representing the 2D model or projection of 3D model.

The registration of the last injection image and the reference image for therapeutic device navigation (such as a balloon or a stent) possesses some specific aspects. The difficulty of registration between last injection image and reference image results from changes in the imaging conditions, as well as changes in the shape of artery caused by the guide wire insertion and other changes between the diagnostic and the navigation stages. The preferred registration scheme adopts a multi level iterative approach of coarse to fine, global to local registration, including a method of constrained correlation achieving accurate result even under condition of severe distortions between the images. The registration process utilizes a multi resolution pyramid representation of the reference and the last injection images, and the application of feature enhancing filtering, such as vessel resemblance map generation for different resolution levels. The registration starts with constrained correlation on coarse pyramidal level, covering a larger area. Then a fine registration is carried out using repeating correlations in the smaller neighborhood of the stenosis region, for higher resolution levels and smaller correlation windows. The process preferably uses correlation windows centered at the stenosis point, or multiple series of correlation windows centered along the reference artery centerline. Another variant of the fine registration is to use a process of automatic identification of the vessel segment in the last injection image, using the coarse registration and the known reference vessel segment. The process yields calculation of centerline and diameter of the vessel along the centerline, on the last injection image. Then the correlation between two one-dimensional diameter functions, one function relating to the last injection image and the other relating to the reference image is determined. The correlation can then be used for matching the centerlines and establishing local transformation between the images. At step 420, elements from both images are fused into one image.

Figure 6:
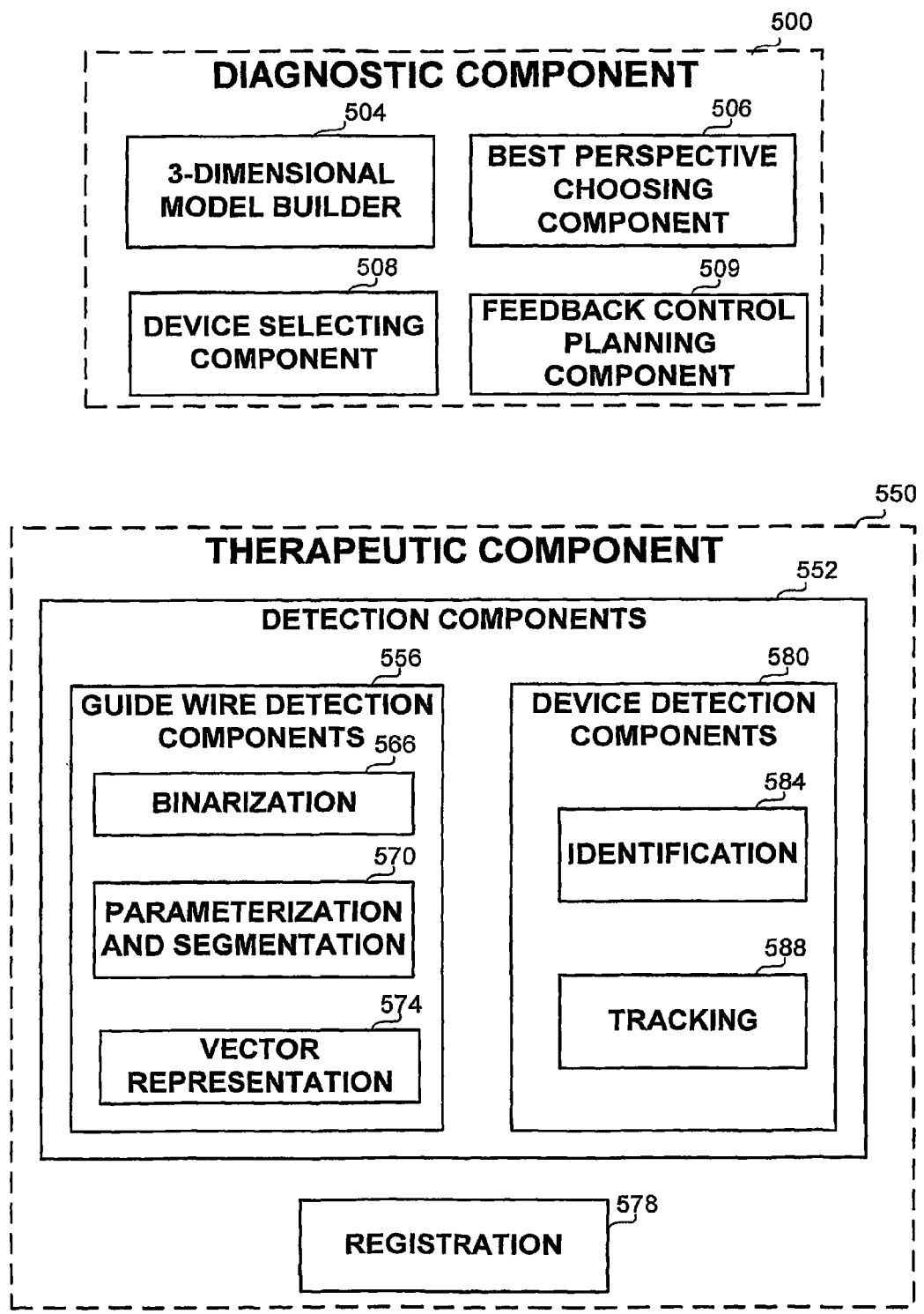
FIG. 6 is a block diagram of the components of the application, in accordance with a preferred embodiment of the present invention.

Referring now to FIG. 6, depicting the operating components of the guide wire and device guidance application which is a preferred embodiment of this invention. A diagnostic stage component 500 is responsible for processing the images acquired during a diagnostic and disease assessment stage.

Diagnostic stage component 500 comprises a 3-dimensional model builder 504, a best perspective choosing component 506, a device selection component 508, and a feedback control planning component 509. The tasks of component 500 and its sub-components are achieved by steps 254, 258 of the method presented in association with FIG. 3 above. Alternatively, component 504 can be omitted, provided the 3-dimensional model is obtained from an external source. A therapeutic stage component 550 comprises detection component 552 and registration component 578. The operation of registration component 578 is detailed in association with FIG. 5 above. Detection components 552 comprise guide wire detection components 556 related to guide wire detection and device detection components 580, handling tasks related to a therapeutic device detection. Device detection components 580 further comprise identification component 584 and tracking component 588. The detection components are being activated according to the used equipment. Guide wire detection component 556 and registration component 578 are preferably implemented as a hybrid process, where registration component 578 is being activated between the activations of different components of detection component 556, but for clarity purposes the components are described separately. When detecting a guide wire, guide wire detection components 556 are being activated. Guide wire detection components 556 comprise a binarization component 566, which is responsible for performing binarization over the current image. Binarization is assigning a value of 1 to all pixels in the picture which have a value exceeding a predetermined threshold, and assigning a value of 0 to all other pixels. Preferably, the binarization is performed on the current image after a fast preprocessing for enhancing the guide wire tip. Normally, as a result of the binarization, one or a few clusters relating to the guide wire tip are distinguished, together with a number of small additional clusters spread over the image. Using the obtained binary image, a coarse registration to the last injection or reference image is performed, using registration component 578. Since the guide wire is known to be located inside a tubular organ such as a vessel, the registration can be performed, for example, by correlation of the guide wire tip segments with a vessel enhanced last injection or reference image or a corresponding binary image presenting the vessel relevant segment. As a result of the coarse registration, a translation of the current image to the reference image is obtained.

Parameterization and segmentation component 570 performs a parameterization of the pixels relatively to the centerline of the artery segment. The centerline of the artery segment is a part of the model of the body part built during the diagnostic step, or received from an external source. Specifically, each pixel in the reference image is assigned two parameters: The first parameter is the shortest distance between the pixel and the centerline of the artery. The second parameter is the index of the pixel in the centerline which is the closest to the pixel under discussion. Since the centerline is indeed a line, its pixels can be ordered and indexed. The parameterization calculations can be carried out on the diagnostic stage or once a synthetic reference image is created. Using the translation between the reference image and the current image found by the coarse registration, the parameters are assigned to the pixels having a value of 1 in the binarized current image. Then, the pixels in the current image are sorted according to the index of the nearest pixel in the centerline and can be presented and treated as a one-dimensional function of the distance from the centerline over the x-axis of centerline point index. The segmentation of the guide wire tip is performed effectively by analyzing this function instead of 2-dimensional image processing. Using the results of segmentation, a region of interest is determined and a local fine registration is performed, again by calling registration component 578. The center point of the guide wire tip, as well as the index in the centerline closest to the center point are obtained. Vector representation component 574 then performs a vector representation of the guide wire tip using a fast algorithm utilizing the suggested parameterization, or using optimal path search techniques on the image plane. Once the detection is complete, the guide wire tip can be shown on the reference image, the 3-dimensional model or other images. Numerical data, such as the direction and curvature of the artery at the guide wire endpoint location, distance to bifurcation, or others, can be provided as well. Once the guide wire is detected, tracking it in the following frames is performed using local registration of a small segment of the image, since the general location of the guide wire tip is known.

Therapeutic device detection component 580 detects the devices using one or more, preferably two markers placed on the device, the markers showing like dark points in an x-ray image. The device is identified in a current image, by identification component 584. First a filtering, enhancing the dark points is used, and then thresholding is performed over all pixels in the image. The filters are, for example Laplacian of Gaussian, filters based on analysis of aigenvalues of Hessian matrix, or the like. This results in clusters of pixels that passed a predetermined threshold values. Normally the marker clusters and few "confuser" clusters are present. The clusters are labeled, assigned with a score that takes into account all scores of pixels in the cluster, and a representative pixel of every cluster is selected. Clusters which are small relatively to other clusters are discarded. The parameters of cluster detection are tuned to minimize the number of detected clusters while preserving the marker clusters. Next, pairs of clusters are considered, since the device is preferably represented in an x-ray image by two markers. Therefore, each pair represents a possibility that the two clusters of the pair indeed represent the two markers. The score assigned to each pair is a product of the two cluster scores. Typically, the pair with the highest score is assumed to represent the markers. However, if an estimation exists for the expected distance between the markers, then the score is multiplied by a function of the ratio between the real distance between clusters and the expected distance. As a further step, the values are normalized to make the sum of all pair estimations be equal to one. However, marker detection based on one frame might be insufficient. Therefore, alternatively two or more successive frames are used. In a one non-limiting example of the current invention, let M denote the number of available pairs in the first frame, and N denote the number of available pairs on the second frame. The probabilities of pairs 1 . . . M to represent the device in the first frame are denoted by $p1, \ldots, pM$ and the probabilities of pairs 1 . . . N to represent the device in the second frame are denoted by $q1, \ldots, qN$. The device markers correspond to two pairs on both frames, therefore a pair of pairs of points is required, i.e., a quartet. In order to locate the correct pair in the first and in the second frame, an M×N matrix R is constructed, where the (i,j) element is r(i,j) =$p_i$*$q_j$*$f(i,j)$, where $f(i,j)$ is some function describing the similarity between the i-th pair on the first frame and the j-th pair on the second frame. In particular $f(i,j)$ reflects how the distance between the points in the pair is preserved. The r(i,j) criterion filters out incorrect pairs. Other components of the r(i,j) function may include the cluster sizes and distances to the a reference skeleton.

If the total sum of the elements of matrix R is below a predetermined threshold, the pair of frames is declared to be inconsistent, and discarded. If the two frames constitute a part of a longer process with no definite conclusions, the process is reset. If the total sum of the elements of matrix R is above the predetermined threshold, the probabilities for pair i in one of the frames to represent the markers is estimated by:

$$q_j(\text{back}) = \sum_{i=1}^{M} r(i, j).$$

i.e., the probability that pair i of clusters in the first frame represents the markers is equal to the sum of probabilities that this pair corresponds to all other pairs in the following frame.

Similarly for pair j in the second frame, in relation to the first frame $$p_i == \frac{p_i(\text{forward}) * q_i(\text{back})}{\sum_{k=1}^{N} p_k(\text{forward}) * q_k(\text{back})}$$

Thus, on each frame in the middle of a sequence there are therefore two additional estimations for each pair of clusters, one marked with "forward", obtained through comparison to the following frame, and another, marked with "back", obtained through comparison to the closest former frame. When we have the sequence of fluoro frames, for each frame, beginning from the second, we may use the estimation for the pairs $q_j$ (back), instead of $q_j$, thus accumulating the information from the previous frames. In a similar way starting from the last frame we may use $p_i$ (forward) instead of $p_i$ Then, for each pair in each frame, the two estimations are combined into one:

$$p_i(\text{forward}) = \sum_{j=1}^{N} r(i, j)$$

Then, if for some pair l, $p_l$ exceeds a predetermined confidence threshold, the markers are declared to be represented by pair l.

The preferred process starts by analyzing two adjacent fluoroscopic frames. If markers are identified (for one pair l in one of the frames, $p_l$ exceeds the predetermined threshold) the process is terminated. Otherwise, the process is generalized by adaptation to considering an additional fluoroscopic frame to the sequence and $p_l$ values are recalculated for the three frames, using the described process. If markers are not identified, another additional frame is added. If after adding a predetermined number of frames, markers identification is not achieved, the sequence is discarded and the process is initialized with a new pair of frames.

Therapeutic device tracking component 588 is activated once a definite recognition of the device is achieved. The system switches to tracking the device, which is a task that requires less processing power and therefore performed in real-time. In order to be effective, tracking a device should take less time than the period between the acquisitions of two consecutive images. Tracking is performed by analyzing successive frames and tracking the identified markers. On the tracking phase, the component receives a current frame Fc where the two markers are to be found and a previous frame Fp with known marker coordinates M1 and M2. Small areas Wp1 and Wp2 around locations M1 and M2 are selected on image Fp and larger areas Wc1 and Wc2 around the locations M1, M2 are selected on image Fc. The radius of the large areas estimates a maximal possible marker movement between frames Fp and Fc. Areas Wp1, Wp2, Wc1 and Wc2 preferably pass preprocessing filtering enhancing dot-like features, for example, Laplacian of Gaussian filter, filters based on analysis of aigenvalues of Hessian matrix, or the like. Then correlations between Wp1 and Wc1 and the correlation between Wp2 and Wc2 are performed. Preferably normalized correlation, phase correlation or gradient vector field correlation are used, but the correlation is not limited to a specific type. As a result, two correlation surfaces C1 and C2 are obtained. Peaks on the correlation surfaces represent areas within Wc1 and Wc2 that are candidates to be the current location of the markers. Let T=(t1, t2, . . . , tn) denote the set of prominent local maxima found on C1 and S=(s1, s2, . . . , sm) denote the set of prominent local maxima found on C2. Every peak has a score equal to the corresponding correlation values $C1(t_i)$ and $C2(s_j)$. Every pair (ti,sj) of possible shifts of the two markers from the previous image to the current image passes a test for a movement consistency criterion giving a pair score $V(t_i,s_j)$. In particular $V(t_j,s_j)$ can be a measure of difference between vectors M2−M1 and $s_j-t_i$, i.e. the distance and direction of the location of the markers should be preserved between the frames. Every pair gets an aggregated score combining $C1(t_i)$, $C2(s_j)$ and $V(t_i,s_j)$, for example $p_i=(C(t_i)+C2(s_j))*V(t_i,s_j)$. The pair that obtained the maximal aggregated score is identified as the shifts of the markers and the markers locations on the current frame are calculated using the previous locations and the shifts. As mentioned above, binary images showing the tracked device are used in the registration process, as the device enhanced image (D1) discussed in association with FIG. 5 above.

As mentioned above, the present invention uses an improved vessel resemblance operator IVR(p). The conventional vessel resemblance operator VR(p) uses the aigenvalues of the Hessian matrix to enhance the pixels p, where the gray levels have a large positive second derivative in one direction and a small second derivative in the orthogonal direction. In order to better discriminate tubular features like vessels, from step-like features (such as, for example boundary of diaphragm) an improved vessel resemblance operator is used, requiring small gradient in addition to the properties of the second derivatives, as detailed above. The additional gradient term in the expression for the improved vessel resemblance IVR(p) might have, for example the following form: IVR(p)=VR(p)·F(|g|), Where F(|g|) is equal to 1 for a zero gradient magnitude |g|, and decreases as the gradient magnitude increases.

The proposed invention discloses a method and apparatus for positioning a device in a tubular organ. The invention discloses an optional diagnostic stage in which a model of the tubular organ is constructed, and a therapeutic device and a location for the device are recommended to the physician. Alternatively, the user can receive a model from an external source. Then, at a therapeutic stage, the apparatus employs the method to automatically register images captured during the therapeutic stage with the model, thus supporting detecting, tracking, navigating the device within the tubular organ. The system further enables displaying the device within the tubular organ along with relevant measurement data. The proposed method overcomes difficulties in the registration, resulting from geometric distortions and differences in content between images taken at the diagnostic stage and images taken at a therapeutic stage. The apparatus uses x-ray or another imaging modality during the therapeutic stage, although most tubular organs, such as vessels are not visible in x-ray images. The system does not require additional equipment in excess of the equipment currently required for the relevant types of procedures. Additionally, the system minimizes the need for harmful contrast material injections and radiations to the subject.

The proposed system uses x-ray images, in which the tubular organ is not visible during the therapeutic stage. However, other modalities can be used as well. If a modality that does show the tubular organ is used, the process will be greatly simplified. The description of the components presented above suggests a possible implementation. It is clear that multiple other divisions of the system into components, which perform different parts of the methods and cooperate in different ways, can be employed as well. It will be appreciated by persons skilled in the art that the present invention is not limited to what has been particularly shown and described hereinabove. Rather the scope of the present invention is defined only by the claims which follow.

What is claimed is:

1. A method for automatic registration of an at least one captured image of a device located inside a tubular organ of a subject with a reference image of a body area of the subject containing the tubular organ, the method comprising the steps of:
   generating a first enhanced background image from the captured image and a second enhanced background image from the reference image, said first and second enhanced background images comprise background elements present in both captured and reference images;
   generating an enhanced tubular organ image from the reference image;
   generating an enhanced device image from the captured image;
   calculating a first correlation surface between said first and second enhanced background images;
   calculating a second correlation surface between said enhanced tubular organ image and said enhanced device image;
   calculating a combined correlation surface as a function of said first and second correlation surfaces; and
   performing registration between the currently captured image and the reference image in accordance with said combined correlation surface, thereby obtaining current location of the device in the tubular organ.

2. The method of claim 1 wherein the device is a guide wire or a therapeutic device.

3. The method of claim 1 wherein the tubular organ is a blood vessel.

4. The method of claim 1 wherein the tubular organ is not visible on the captured image.

5. The method of claim 1 wherein the captured image is an X-ray image.

6. The method of claim 1 wherein the reference image is an angiogram.

7. The method of claim 1 wherein the captured image and the reference image are taken at substantially the same projection angle.

8. The method of claim 1 wherein the reference image is acquired at a diagnostic stage before said device is located inside said tubular organ.

9. The method of claim 1 further comprising a step of generating the reference image from a pre-acquired three-dimensional model of the body area containing the tubular organ by projecting the model at substantially the same projection angle as of the captured image.

10. The method of claim 9 wherein said pre-acquired three-dimensional model is constructed from at least two angiograms taken at two different projection angles.

11. The method of claim 10 wherein the reference image is one of said at least two angiograms.

12. The method of claim 9 wherein said pre-acquired three-dimensional model is a model constructed from Computerized Tomography (CT) volumetric data.

13. The method of claim 1 wherein said reference image is a mediating image obtained by injecting a contrast material to the tubular organ when said device is already present in the tubular organ and wherein the method comprises a further step of performing registration between the mediating image and a pre-acquired reference image of the body area containing the tubular organ, said pre-acquired reference image is acquired at a diagnostic stage before the device is located inside the tubular organ.

14. The method of claim 1 further comprising a step of displaying information derived from said registration, said information comprises a fused image containing at least one element from the group consisting of: captured image; at least one element from the reference image; the device and the tubular organ in a common coordinate system;
   data relating to the distance between a current location of the device and a predetermined location,
   wherein the predetermined location is the designated location of the device or a landmark designated during a diagnostic stage;
   and direction or curvature of the tubular organ at the current location of the device.

15. The method of claim 1 wherein the enhanced tubular organ image is prepared from the reference image by using a vessel resemblance operator, wherein the vessel resemblance operator is an improved vessel resemblance operator that incorporates a requirement for a small gradient.

16. The method of claim 1 wherein the step of generating the enhanced device image comprises the step of:
   detecting the device within the captured image, wherein detecting the device comprises:
   identifying the device; and
   tracking the device.

17. The method of claim 16 wherein the device is a guide wire and wherein detecting the guide wire within the captured image comprises the steps of:
   performing a binarization of the captured image to obtain a binarized image of the guide wire;
   performing parameterization of the reference image relatively to a center line of the tubular organ so as assign to each pixel in the reference image a set of parameters;
   performing a first registration of the binarized image with the reference image;
   assigning to detected pixels in the binarized image the set of parameters from the corresponding pixels in the reference image;
   sorting the pixels according to their assigned set of parameters; and segmenting the guide wire tip by analyzing the sorted pixels.

18. The method of claim 17 further comprising the step of performing a vector representation of the guide wire.

19. The method of claim 16 wherein the device is a therapeutic device having at least two radio-opaque markers and wherein the identifying step comprises:
   (a) thresholding substantially all pixels in the captured image to receive at least one cluster;
   (b) assigning a score to each of the at least one cluster;
   (c) assigning a score to each pair of clusters;
   (d) if the highest score assigned at step (c) to a pair of clusters exceeds a predetermined threshold, selecting the pair of clusters as the device markers.

20. The method of claim 19 further comprising:
   (e) executing steps (a) to (d) for a second captured image;
   (f) creating quartets of clusters, where the first pair of clusters is taken from the clusters received from the captured image, and the second pair of clusters is taken from the second captured image;
   (g) assigning a score to each quartet of clusters, the score comprising the score of each pair and a similarity factor between the pairs;
   (h) assigning a second score to each pair of clusters in the captured image, based on the scores for all quartets in which the pair of clusters participates;
   (i) assigning a second score to each pair of clusters in the second captured image, based on the scores of all quartets in which the pair of clusters participates; and
   (j) if the highest score assigned at step (i) to a pair of clusters exceeds a predetermined threshold, selecting the pair of clusters as the markers in the captured image or in the second captured image.

21. The method of claim 16 wherein the device is a therapeutic device and wherein the tracking step comprises using at least two correlation surfaces between two consecutive captured images and an at least one movement consistency criterion.

22. An apparatus for automatic registration and detection of an at least one captured image of a device located inside a tubular organ of a subject with a reference image of a body area of the subject containing the tubular organ, the apparatus comprising:

an image acquisition unit for receiving an at least one captured image of a device located inside a tubular organ;
at least one detection device for identifying and tracking the device in said at least one captured image and for generating a device enhanced image;
a processor, said processor comprising:
   a vessel resemblance operator for generating an enhanced image of said tubular organ from the reference image;
   an image background enhancing component for generating enhanced background images from said captured image and reference image; and
   a combined correlation computation component for calculating a combined correlation surface as a function of a first correlation surface between said enhanced background images of the captured and the references image and a second correlation surface between said enhanced device image and said enhanced image of the tubular organ.

23. A navigation system for navigating a device inside a tubular organ and for positioning the device in a designated location, the system comprising the apparatus of claim 22 for detecting and tracking the device during a therapeutic stage and the processor further comprising a diagnostic stage component, the diagnostic stage component comprises a device selecting component for allowing a physician to choose a therapeutic device and a designated location of the device, and a best perspective choosing component for selecting a position of a C-arm best for the therapeutic stage.

24. The navigation system of claim 23 further comprising a 3-dimensional model builder for reconstructing the body area containing the tubular organ from two or more 2-dimensional images and for analyzing the tubular organ to obtain information relevant to the tubular organ.

25. The navigation system of claim 23 further comprising a feedback control system for automatically controlling the advancement or the shape of the device in accordance with information received from said apparatus.

* * * * *